United States Patent [19]

Wiezer et al.

[11] 4,247,449
[45] Jan. 27, 1981

[54] UREA DERIVATIVES, PROCESS FOR THEIR MANUFACTURE AND THEIR USE AS LIGHT PROTECTING AGENTS FOR POLYMERS

[75] Inventors: Hartmut Wiezer, Gersthofen; Norbert Mayer, Gablingen; Harald Knorr, Gersthofen, all of Fed. Rep. of Germany

[73] Assignee: Hoechst Aktiengesellschaft, Fed. Rep. of Germany

[21] Appl. No.: 62,468

[22] Filed: Jul. 31, 1979

[30] Foreign Application Priority Data

Aug. 5, 1978 [DE] Fed. Rep. of Germany ...... 2834455

[51] Int. Cl.$^3$ ............... C08K 5/35; C07D 491/10; C07D 491/20
[52] U.S. Cl. ............................ 260/45.8 NZ; 546/19
[58] Field of Search ................. 260/45.9 NZ; 546/19

[56] References Cited

U.S. PATENT DOCUMENTS

| 4,107,139 | 8/1978 | Mayer et al. ............. 260/45.8 NZ |
| 4,110,334 | 8/1978 | Mayer et al. ............. 260/45.8 NZ |

FOREIGN PATENT DOCUMENTS

| 1770689 | 11/1971 | Fed. Rep. of Germany . |
| 1769646 | 3/1972 | Fed. Rep. of Germany . |
| 2500313 | 7/1975 | Fed. Rep. of Germany . |
| 2606026 | 8/1977 | Fed. Rep. of Germany . |
| 2738340 | 3/1979 | Fed. Rep. of Germany ......... 546/19 |

Primary Examiner—V. P. Hoke
Attorney, Agent, or Firm—Connolly and Hutz

[57] ABSTRACT

The amide nitrogen of 9,9-dimethyl-2-oxa-4-oxo-3,8-diazaspiro-(4,5)-decane reacts with isocyanates or diisocyanates to give novel urea derivatives which can be used as light stabilizers for plastic materials.

5 Claims, No Drawings

UREA DERIVATIVES, PROCESS FOR THEIR MANUFACTURE AND THEIR USE AS LIGHT PROTECTING AGENTS FOR POLYMERS

This invention relates to novel urea derivatives, to a process for their manufacture and to their use for stabilizing synthetic polymers against the detrimental influence of light.

The novel urea derivatives derive from 9,9-dimethyl-1-oxa-4-oxo-3,8-diazaspiro(4,5)decane and correspond to the formula I

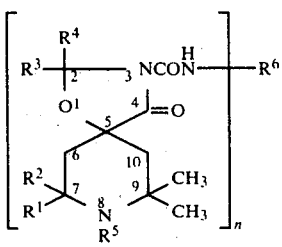

in which
- $R^1$ and $R^2$ denote identical or different straight chain or branched alkyl radicals having from 1 to 12, preferably 1 to 6, carbon atoms, especially methyl; or $R^1$ and $R^2$ together with the carbon atoms to which they are linked denote an optionally methyl-substituted cyclopentane or cyclohexane ring or a 2,2,6,6-tetramethylpiperidine ring carbon atoms 4 of which is identical with carbon atom 7 of the spirodecane system;
- $R^3$ denotes hydrogen, alkyl or isoalkyl having from 1 to 30, preferably 1 to 10 and more preferably 1 to 6, carbon atoms, or aralkyl having from 7 to 10 carbon atoms with 1 to 4 carbon atoms in the aliphatic chain;
- $R^4$ denotes hydrogen, alkyl having from 1 to 30, preferably 1 to 17 and more preferably 1 to 11, carbon atoms, phenyl or naphthyl optionally substituted by a halogen atom, preferably chlorine, or alkyl having from 1 to 4 carbon atoms, or denotes aralkyl with 7 to 10 carbon atoms with 1 to 4 carbon atoms being in the aliphatic chain;
- $R^3$ and $R^4$ may also be together with the carbon atom by which they are linked a cycloalkane ring having from 4 to 20, preferably 5 to 12 and more preferably 5 to 7, carbon atoms which may be substituted by 1 or 2 $C_1$ to $C_4$ alkyl radicals;
- $R^5$ denotes hydrogen, oxygen or $C_1$–$C_4$ alkyl, preferably hydrogen or methyl and more preferably hydrogen;
- $R^6$, with n being 1, denotes alkyl having from 1 to 20, preferably from 4 to 18, carbon atoms, alkenyl having from 2 to 18 carbon atoms, cycloalkyl having from 5 to 12, preferably 5 to 7 and more preferably 6, carbon atoms which may be substituted by a $C_1$–$C_4$ alkyl radical; phenyl or naphthyl optionally substituted by a chlorine atom or alkyl having from 1 to 18, preferably 1 to 4, carbon atoms; or phenylalkyl having from 7 to 18, preferably 7 to 10, carbon atoms, or
- $R^6$, with n being 2, denotes a straight chain or branched alkylene group having from 2 to B 20, preferably 2 to 12 and more preferably 2 to 6, carbon atoms, or phenylene or naphthylene optionally substituted by $C_1$–$C_4$ alkyl, or a diphenylenealkane radical having from 13 to 18 carbon atoms.

The nitrogen atom in position 8 or the ring has basic properties when it is substituted by hydrogen or alkyl, and, therefore, the compounds in these cases may also be in the form of salts with inorganic or organic acids.

Radicals $R^1$ and $R^2$ denote for example, methyl, ethyl or isobutyl and radicals in which $R^1$ and $R^2$ form a ring together with the carbon atom to which they are bound are, for example, cyclopentyl, cyclohexyl or 2,2,6,6-tetramethyl-piperididyl.

Examples of $R^3$ are hydrogen, methyl, ethyl, propyl, butyl, pentyl, hexyl, heptyl, benzyl, examples for $R^4$ are hydrogen, methyl, ethyl, propyl, isopropyl, butyl, isobutyl, pentyl, isopentyl, hexyl, isohexyl, heptyl, isoheptyl, octyl, isooctyl, nonyl, isononyl, decyl, isodecyl, undecyl, dodecyl, tridecyl, benzyl, phenyl, chlorophenyl, phenylethyl.

Examples for those cases in which $R^3$ and $R^4$, together with carbon atom 2 of the ring to which they are linked, form a cycloalkyl ring are cyclopentyl, cyclohexyl, methylcyclohexyl, cycloheptyl and cyclododecyl.

$R^5$ denotes, for example hydrogen and lower alkyl, preferably methyl.

In compounds with n=1 (monoisocyanates) $R^6$ denotes for example methyl, ethyl, propyl, butyl, isobutyl, octadecyl, cyclohexyl, phenyl, 3-chlorophenyl, 4-chlorophenyl, 3-methylphenyl, 4-methylphenyl, 1-naphthyl.

In compounds with n=2 (diisocyanates) $R^6$ denotes for example, ethylene, hexamethylene, diphenylene methane, 4-methyl-m-phenylene.

Examples of possible salts of the compounds of formula I are those with non-oxidizing inorganic acids, such as phosphates, phosphites, chlorides, sulfates and salts with organic mono- and polycarboxylic acids, such as acetates, laurates, stearates, succinates, sebacates, maleates, citrates, tartrates, oxalates, benzoates, sulfonates, phosphonates. The salts are prepared by combining equivalent amounts of acid and base, each dissolved in a solvent, and evaporating the solvent.

From among the novel urea derivatives the following are named by way of example:

2,2,7,7,9,9-hexamethyl-3-propyl-carbamoyl-1-oxa-4-oxo-3,8-diaza-spiro-(4,5)-decane;
2,2,7,7,9,9-hexamethyl-3-butyl-carbamoyl-1-oxa-4-oxo-3,8-diaza-spiro-(4,5)-decane;
2,2,7,7,9,9-hexamethyl-3-tert.-butyl-carbamoyl-1-oxa-4-oxo-3,8-diaza-spiro-(4,5)-decane;
2,2,7,7,9,9-hexamethyl-3-octadecyl-carbamoyl-1-oxa-4-oxo-3,8-diaza-spiro-(4,5)-decane;
2,2,7,7,9,9-hexamethyl-3-cyclohexyl-carbamoyl-1-oxa-4-oxo-3,8-diaza-spiro-(4,5)-decane;
2,2,7,7,9,9-hexamethyl-3-phenyl-carbamoyl-1-oxa-4-oxo-3,8-diaza-spiro-(4,5)-decane;
2,2,7,7,9,9-hexamethyl-3-m-chlorophenyl-carbamoyl-1-oxa-4-oxo-3,8-diaza-spiro-(4,5)-decane;
2,2,7,7,9,9-hexamethyl-3-p-chlorophenyl-carbamoyl-1-oxa-4-oxo-3,8-diaza-spiro-(4,5)-decane;
2,2,7,7,9,9-hexamethyl-3-α-naphthyl-carbamoyl-1-oxa-4-oxo-3,8-diaza-spiro-(4,5)-decane;
2-butyl-7,7,9,9-tetramethyl-3-octadecyl-carbamoyl-1-oxa-4-oxo-3,8-diaza-spiro-(4,5)-decane;
2-iso-pentyl-7,7,9,9-tetramethyl-3-cyclohexyl-carbamoyl-1-oxa-4-oxo-3,8-diaza-spiro-(4,5)-decane;
2-iso-nonyl-7,7,9,9-tetramethyl-3-butyl-carbamoyl-1-oxa-4-oxo-3,8-diaza-spiro-(4,5)-decane;

2-undecyl-7,7,9,9-tetramethyl-3-octadecyl-carbamoyl-1-oxa-4-oxo-3,8-diaza-spiro-(4,5)-decane;
2-phenyl-7,7,9,9-tetramethyl-3-phenyl-carbamoyl-1-oxa-4-oxo-3,8-diaza-spiro-(4,5)-decane;
2-phenyl-7,7,9,9-tetramethyl-3-octadecyl-carbamoyl-1-oxa-4-oxo-3,8-diaza-spiro-(4,5)-decane;
2-propyl-2,7,7,9,9-pentamethyl,3-propyl-carbamoyl-1-oxa-4-oxo-3,8-diaza-spiro-(4,5)-decane;
2-iso-butyl-2,7,7,9,9-pentamethyl-3-cyclohexyl-carbamoyl-1-oxa-4-oxo-3,8-diaza-spiro-(4,5)-decane;
2-iso-octyl-7,7,9,9-tetramethyl-3-cyclohexyl-carbamoyl-1-oxa-4-oxo-3,8-diaza-spiro-(4,5)-decane;
2-nonyl-2,7,7,9,9-pentamethyl-3-octadecyl-carbamoyl-1-oxa-4-oxo-3,8-diaza-spiro-(4,5)-decane;
2,2-diethyl-7,7,9,9-tetramethyl-3-butyl-carbamoyl-1-oxa-4-oxo-3,8-diaza-spiro-(4,5)-decane;
2,2-diethyl-7,7,9,9-tetramethyl-3-cyclohexyl-carbamoyl-1-oxa-4-oxo-3,8-diaza-spiro-(4,5)-decane;
2,2-diethyl-7,7,9,9-tetramethyl-3-octadecyl-carbamoyl-1-oxa-4-oxo-3,8-diaza-spiro-(4,5)-decane;
2,2-diethyl-7,7,9,9-tetramethyl-3-phenyl-carbamoyl-1-oxa-4-oxo-3,8-diaza-spiro-(4,5)-decane;
2,2-dipropyl-7,7,9,9-tetramethyl-3-butyl-carbamoyl-1-oxa-4-oxo-3,8-diaza-spiro-(4,5)-decane;
2,2-dibutyl-7,7,9,9-tetramethyl-3-octadecyl-carbamoyl-1-oxa-4-oxo-3,8-diaza-spiro-(4,5)-decane;
2-ethyl-2-pentyl-7,7,9,9-tetramethyl-3-cyclohexyl-carbamoyl-1oxa-4-oxo-3,8-diaza-spiro-(4,5)-decane;
2,2-dibenzyl-7,7,9,9-tetramethyl-3-phenyl-carbamoyl-1-oxa-4-oxo-3,8-diaza-spiro-(4,5)-decane;
2,2,4,4-tetramethyl-14-butyl-carbamoyl-7-oxa-3,14-diaza-15-oxo-dispiro-(5,1,5,2)-pentadecane;
2,2,4,4-tetramethyl-14-cyclohexyl-carbamoyl-7-oxa-3,14-diaza-15-oxo-dispiro-(5,1,5,2)-pentadecane;
2,2,4,4-tetramethyl-14-phenyl-carbamoyl-7-oxa-3,14-diaza-15-oxo-dispiro-(5,1,5,2)-pentadecane;
n-hexane-1',6'-bis-[3-carbamoyl-2,2,7,7,9,9-hexamethyl-1-oxa-4-oxo-3,8-diaza-spiro-(4,5)-decane];
toluylene-2',4'-bis-[3-carbamoyl-2,2,7,7,9,9-hexamethyl-1-oxa-4-oxo-3,8-diaza-spiro-(4,5)-decane];
n-hexane-1',6'-bis-[14-carbamoyl-2,2,4,4-tetramethyl-7-oxa-3,14-diaza-15-oxo-dispiro-(5,1,5,2)-pentadecane];
toluylene-2',4'-bis-[14-carbamoyl-2,2,4,4-tetramethyl-7-oxa-3,14-diaza-15-oxo-dispiro-(5,1,5,2)-pentadecyl];
n-hexane-1',6'-bis-[20-carbamoyl-2,2,4,4-tetramethyl-7-oxa-3,20-diaza-21-oxo-dispiro-(5,1,11,2)-heneicosane];
toluylene-2',4'-bis-[20-carbamoyl-2,2,4,4-tetramethyl-7-oxa-3,20-diaza-21-oxo-dispiro-(5,1,11,2)-heneicosane];
n-hexane-1',6'-bis-[3-carbamoyl-2,2-diethyl-7,7,9,9-tetramethyl-1-oxa-4-oxo-3,8-diaza-spiro-(4,5)-decane];
toluylene-2',4'-bis-[3-carbamoyl-2,2-diethyl-7,7,9,9-tetramethyl-1-oxa-4-oxo-3,8-diaza-spiro-(4,5)-decane];
n-hexane-1',6'-bis-[3-carbamoyl-2-iso-octyl-7,7,9,9-tetramethyl-1-oxa-4-oxo-3,8-diaza-spiro-(4,5)-decane];
toluylene-2',4'-bis-[3-carbamoyl-2,2-diethyl-7,7,9,9-tetramethyl-1-oxa-4-oxo-3,8-diaza-spiro-(4,5)-decane];
n-hexane-1',6'-bis-[3-carbamoyl-2-iso-octyl-7,7,9,9-tetramethyl-1-oxa-4-oxo-3,8-diaza-spiro-(4,5)-decane].

The different nomenclature of some of the compounds listed above results from the IUPAC regulations (cf. Hellwinkel, "Die systematische Nomenklatur der organischen Chemie"; Spinger-Verlag, Heidelberg).

The novel compounds of formula I are produced by reacting substituted piperidines of the formula III, obtainable by the process disclosed in German Offenlegungsschrift No. 2,606,026, with isocyanates or diisocyanates of the formula II. The reaction is illustrated by the following equation:

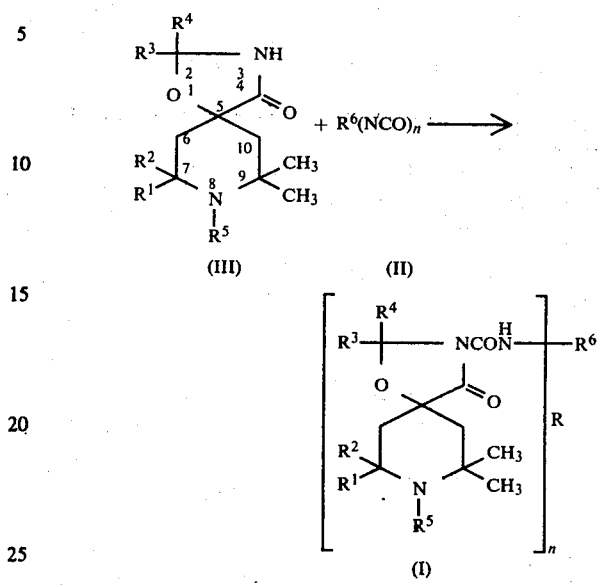

in which $R^1$, $R^2$, $R^3$, $R^5$ and $R^6$ are as defined above and n is 1 or 2 according to the functionality of the isocyanate. It is especially surprising that compounds of formula III in which $R^5$ denotes hydrogen also react with the isocyanates in the manner indicated above and not at the amine nitrogen in position 8.

To carry out the reaction the piperidine derivative is dissolved in an inert organic solvent, a catalytic amount of a strong base, for example 1,4-diazabicyclooctane is added, the equivalent amount of the isocayanate, optionally in the same solvent, is added dropwise and the mixture is allowed to react at 20° to 180° C., preferably 20° to 140° C. and more preferably 50° to 120° C. The reaction time is from 1 to 30 and preferably 4 to 20 hours.

Suitable inert organic solvents are, for example, heptane, aliphatic hydrocarbon fractions having a boiling temperature of up to 180° C., toluene, xylene, diethyl ether, dioxane, halo-hydrocarbons such as chloroform, carbon tetrachloride and chlorobenzene, preferably, however, toluene.

Difficulty soluble reaction products are separated by filtration, while with dissolved products the solvent is evaporated and the remaining reaction product is purified by recrystallization.

The novel urea derivatives are excellently suitable for stabilizing synthetic polymers against the decomposing action of light. Synthetic polymers in the sense of the present specification are halogen-free and halogen-containing homo- and copolymers, more particularly homopolymers of olefins, dienes and styrene, such as for example, polyethylene of low and high density, polypropylene, polystyrene, polybutadiene and polyisoprene; copolymers of olefins, dienes and styrene with one another or with other olefinically unsaturated monomers, such as, for example, ethylene-propylene copolymers, ethylene-butene copolymers, styrene-butadiene copolymers, ethylene-vinyl acetate copolymers and acrylonitrile and acrylonitrile-butadienestyrene copolymers, homopolymers of vinyl chloride and vinylidene chloride as well as copolymers of the said monomers with one another and with other olefinically unsaturated monomers. The term synthetic polymer is also intended to include polyurethanes, polyacetals, polyesters, polyamides, polyacrylates and epoxide resins. Especially good results are obtained with poly-α-olefins such as polyethylenes and preferably polypropylenes and with vinyl chloride polymers.

It is surprising and could not have been foreseen that the compounds according to the invention are distinctly superior in their UV stabilizing effect to compounds as described in German Offenlungungsschrift Nos. 2,500,313; 1,770,689 and 1,769,646 having similar structures, i.e. ureas or spirodecanes with similar basic skeleton. Rather, it could be supposed that, due to the insignificant modifications of the structure, the compounds would have the same effect or even a somewhat inferior effect and, owing to their polarity, would exhibit a poorer compatibility, especially with non polar polymers, for example polyolefins.

The novel compounds with stabilizing effect are incorporated into the polymer mass by customary methods. Alternatively, a solution, suspension or emulsion of the stabilizer can be mixed with the polymer per se or with a solution, suspension or emulsion thereof, whereupon the solvent is removed.

The stabilizers according to the invention can be used either alone or in admixture with one or several stabilizers generally used in plastics processing, for example antioxydants on phenol and sulfide basis, UV absorbers and light protecting agents, phosphite stabilizers, metal compounds, epoxide stabilizers and polyhydric alcohols. The plastics compositions to be stabilized may further contain flame retardants and pigments, dyestuffs, antistatic agents and fillers, for example glass fibers.

Examples of suitable antioxydants are those of the type of sterically hindered phenols, for example 2,6-di-tert.butyl-p-cresol, 2,6-dioctadecyl-p-cresol, 4,4'-butylidene-bis(2,6-di-tert.butyl-phenol), 4,4'-thio-bis(2-tert.butyl-5-methyl-phenol), phenolic triazine compounds, thiodipropionic acid esters of fatty alcohols, dioctadecyl sulfide and disulfide.

UV absorbers and light protecting agents to be used are, for example, 2-(2'-hydroxyphenyl)-benztriazoles such as 2-(2'-hydroxy-5'-methylphenyl)-benztriazole, 2-hydroxybenzophenones such as 2-hydroxy-4-octoxybenzophenone, stabilizers of the salicylate group such as octylphenyl salicylate, nickel chelates, oxalic acid diamides and sterically hindered piperidine compounds.

Suitable phosphite stabilizers are trisnonylphenyl phosphite, trislauryl phosphite and esters of pentaerythritol phosphite.

Metal compounds known as stabilizers include calcium, barium, strontium, zinc, cadmium, magnesium, aluminum and lead soaps of aliphatic carboxylic acids or oxycarboxylic acids having about 12 to 32 carbon atoms, salts of the said metals with aromatic carboxylic acids such as benzoates or salicylates as well as (alkyl)-phenolates of the aforesaid metals, organotin compounds, for example di-alkyl-tin thioglycolates and carboxylates.

Known epoxide stabilizers are, for example, epoxidized higher fatty acids, such as epoxidized soybean oil, tall oil, linseed oil, or epoxidized butyl oleate, and epoxides of long chain olefins.

Polyhydric alcohols to be used are, for example, pentaerythritol, trimethylolpropane, sorbitol or mannitol, i.e. preferably alcohols having 5 or 6 carbon atoms and 3 to 6 hydroxy groups.

An efficient stabilizer combination for poly-α-olefins, such a high, medium and low pressure polymers of $C_2$ to $C_4$-α-olefins, especially polyethylene and polypropylene, or copolymers of the said α-olefins consists, for example of 0.01 to 5 parts by weight of a compound according to the invention, 0.05 to 5 parts of a phenolic stabilizer, optionally 0.01 to 5 parts by weight of a sulfur-containing costabilizer, optionally 0.01 to 3 parts by weight of a basic or neutral metal soap, such as calcium stearate or zinc stearate, optionally 0.1 to 5 parts by weight of a phosphite and optionally 0.01 to 5 parts by weight of a known UV stabilizer from the group of alkoxyhydroxybenzophenones, hydroxyphenylbenztriazoles, benzylidene-malonic acid mononitrile esters, or so-called quenchers, for example nickel chelates, all parts being calculated on 100 parts by weight of polymer.

The following examples illustrate the invention. The structures of the compounds obtained were determined by nuclear resonance spectroscopy, their composition was determined by elemental analysis.

EXAMPLE 1

2,2,7,7,9,9-Hexamethyl-3-propyl-carbamoyl-1-oxa-4-oxo-3,8-diaza-spiro-(4,5)-decane 12.0 g (0.05 mol) of 2,2,7,7,9,9-hexamethyl-1-oxa-4-oxo-3,8-diaza-spiro-(4,5)-decane, 4.25 g (0.05 mol) of propyl isocyanate, 0.1 g 1,4-diazabicyclooctane and 100 ml of absolute toluene were refluxed for 15 hours while stirring. The toluene was then distilled off and the residue recrystallized from heptane; m.p. 119° C. stearate m.p. 87° C.; succinate m.p. 169° C.; p.-tert-butylbenzoate m.p. 217° C.

EXAMPLES 2 TO 22

The compounds listed in the following table were prepared under the conditions of Example 1.

TABLE

Examples 2 to 22

| Ex. No. | starting material spiro compound | isocyanate | process product carbamoyl compound | m.p. °C. |
|---|---|---|---|---|
| 2 | 2,2,7,7,9,9-hexamethyl-1-oxa-4-oxo-3,8-diaza-spiro-(4,5)-decane | $C_4H_9NCO$ | 2,2,7,7,9,9-hexamethyl-3-butyl-carbamoyl-1-oxa-4-oxo-3,8-diaza-spiro-(4,5)-decane | 90–93 |
| 3 | 2,2,7,7,9,9-hexamethyl-1-oxa-4-oxo-3,8-diaza-spiro-(4,5)-decane | t.-$C_4H_9NCO$ | 2,2,7,7,9,9-hexamethyl-3-tert.-butyl-carbamoyl-1-oxa-4-oxo-3,8-diaza-spiro-(4,5)-decane | 95 |
| 4 | 2,2,7,7,9,9-hexamethyl-1-oxa-4-oxo-3,8-diaza-spiro-(4,5)-decane | $C_{18}H_{37}NCO$ | 2,2,7,7,9,9-hexamethyl-3-octadecyl-carbamoyl-1-oxa-4-oxo-3,8-diaza-spiro-(4,5)-decane | 51–53 |
| 5 | 2,2,7,7,9,9-hexamethyl-1-oxa-4-oxo-3,8-diaza-spiro-(4,5)-decane | $C_6H_{11}NCO$ | 2,2,7,7,9,9-hexamethyl-3-cyclohexyl-carbamoyl-1-oxa-4-oxo-3,8-diaza-spiro-(4,5)-decane | 123–125 |
| 6 | 2,2,7,7,9,9-hexamethyl-1-oxa-4-oxo-3,8-diaza-spiro-(4,5)-decane | $C_6H_5NCO$ | 2,2,7,7,9,9-hexamethyl-3-phenyl-carbamoyl-1-oxa-4-oxo-3,8-diaza-spiro-(4,5)-decane | 144–147 |
| 7 | 2,2,7,7,9,9-hexamethyl-1-oxa-4-oxo-3,8-diaza-spiro-(4,5)-decane | $(CH_2)_6(NCO)_2$ | n-hexane-1',6'-bis-[3-carbamoyl-2,2,7,7,9,9-hexamethyl-1-oxa-4-oxo-3,8-diaza-spiro-(4,5)- | 191–194 |

TABLE-continued

Examples 2 to 22

| Ex. No. | starting material spiro compound | isocyanate | process product carbamoyl compound | m.p. °C. |
|---|---|---|---|---|
| 8 | 2,2,7,7,9,9-hexamethyl-1-oxa-4-oxo-3,8-diaza-spiro-(4,5)-decane | toluylene-2,4-diisocyanate | toluylene-2',4'-bis-[3-carbamoyl-2,2,7,7,9,9-hexamethyl-1-oxa-4-oxo-3,8-diaza-spiro-(4,5)-decane] | 186 |
| 9 | 2,2-diethyl-7,7,9,9-tetramethyl-1-oxa-4-oxo-3,8-diaza-spiro-(4,5)-decane | $C_4H_9NCO$ | 2,2-diethyl-7,7,9,9-tetramethyl-3-butyl-carbamoyl-1-oxa-4-oxo-3,8-diaza-spiro-(4,5)-decane | 105–108 |
| 10 | 2,2-diethyl-7,7,9,9-tetramethyl-1-oxa-4-oxo-3,8-diaza-spiro-(4,5)-decane | $C_6H_{11}NCO$ | 2,2-diethyl-7,7,9,9-tetramethyl-3-cyclohexyl-carbamoyl-1-oxa-4-oxo-3,8-diaza-spiro-(4,5)-decane | |
| 11 | 2,2-diethyl-7,7,9,9-tetramethyl-1-oxa-4-oxo-3,8-diaza-spiro-(4,5)-decane | $C_6H_5NCO$ | 2,2-diethyl-7,7,9,9-tetramethyl-3-phenyl-carbamoyl-1-oxa-4-oxo-3,8-diaza-spiro-(4,5)-decane | 110–112 |
| 12 | 2,2-diethyl-7,7,9,9-tetramethyl-1-oxa-4-oxo-3,8-diaza-spiro-(4,5)-decane | $(CH_2)_6(NCO)_2$ | n-hexane-1',6'-bis-[3-carbamoyl-2,2-diethyl-7,7,9,9-tetramethyl-1-oxa-4-oxo-3,8-diaza-spiro-(4,5)-decane] | 130–131 |
| 13 | 2,2-diethyl-7,7,9,9-tetramethyl-1-oxa-4-oxo-3,8-diaza-spiro-(4,5)-decane | toluylene-2,4-diisocyanate | toluylene-2',4'-bis-[3-carbamoyl-2,2-diethyl-7,7,9,9-tetramethyl-1-oxa-4-oxo-3,8-diaza-spiro-(4,5)-decane] | 190 |
| 14 | 2-iso-octyl-7,7,9,9-tetramethyl-1-oxa-4-oxo-3,8-diaza-spiro-(4,5)-decane | $C_6H_{11}NCO$ | 2-iso-octyl-7,7,9,9-tetramethyl-3-cyclohexyl-carbamoyl-1-oxa-4-oxo-3,8-diaza-spiro-(4,5-)-decane | 93–97 |
| 15 | 2-iso-octyl-7,7,9,9-tetramethyl-1-oxa-4-oxo-3,8-diaza-spiro-(4,5)-decane | $(CH_2)_6(NCO)_2$ | n-hexane-1',6'-bis-[3-carbamoyl-2-iso-octyl-7,7,9,9-tetramethyl-1-oxa-4-oxo-3,8-diaza-spiro-(4,5)-decane] | waxy |
| 16 | 2,2,4,4-tetramethyl-7-oxa-3,14-diaza-15-oxo-dispiro-(5,1,5,2)-pentadecane | $C_4H_9NCO$ | 2,2,4,4-tetramethyl-14-butyl-carbamoyl-7-oxa-3,15-diaza-15-oxo-dispiro-(5,1,5,2)-petandecane | 103–106 |
| 17 | 2,2,4,4-tetramethyl-7-oxa-3,14-diaza-15-oxo-dispiro-(5,1,5,2)-pentadecane | $C_6H_{11}NCO$ | 2,2,4,4-tetramethyl-14-cyclohexyl-carbamoyl-7-oxa-3,14-diaza-15-oxo-dispiro-(5,1,5,2)-pentadecane | 153 |
| 18 | 2,2,4,4-tetramethyl-7-oxa-3,14-diaza-15-oxo-dispiro-(5,1,5,2)-pentadecane | $C_6H_5NCO$ | 2,2,4,4-tetramethyl-14-phenyl-carbamoyl-7-oxa-3,14-diaza-15-oxo-dispiro-(5,1,5,2)-pentadecane | 156–158 |
| 19 | 2,2,4,4-tetramethyl-7-oxa-3,14-diaza-15-oxo-dispiro-(5,1,5,2)-pentadecane | $(CH_2)_6(NCO)_2$ | n-hexane-1',6'-bis[14-carbamoyl-2,2,4,4-tetramethyl-7-oxa-3,14-diaza-15-oxo-dispiro-(5,1,5,2)-pentadecane] | |
| 20 | 2,2,4,4-tetramethyl-7-oxa-3,14-diaza-15-oxo-dispiro-(5,1,5,2)-pentadecane | toluylene-2,4-diisocyanate | toluylene-2',4'-bis-[14-carbamoyl-2,2,4,4-tetramethyl-7-oxa-3,14-diaza-15-oxo-dispiro-(5,1,5,2)-pentadecane] | 158 |
| 21 | 2,2,4,4-tetramethyl-7-oxa-3,20-diaza-21-oxo-dispiro-(5,1,11,2)-heneicosane | $(CH_2)_6(NCO)_2$ | n-hexane-1',6'-bis-[20-carbamoyl-2,2,4,4-tetramethyl-7-oxa-3,20-diaza-21-oxo-dispiro-(5,1,11,2)-heneicosane] | |
| 22 | 2,2,4,4-tetramethyl-7-oxa-3,20-diaza-21-oxo-dispiro-(5,1,11,2)-heneicosane | toluylene-2,4-diisocyanate | toluylene-2',4'-bis-[20-carbamoyl-2,2,4,4-tetramethyl-7-oxa-3,20-diaza-21-oxo-dispiro-(5,1,11,2)-heneicosane] | |

EXAMPLE 23

This example demonstrates the light stabilizing effect of the compounds according to the invention when used in a poly-α-olefin.

100 parts by weight of polypropylene having a melting index $i_5$ of about 6 g/10 min (determined according to ASTM D 1238-62 T) and a density of 0.96 g/cc were blended with 0.1 part by weight of pentaerythrityl-tetrakis-3-(3,5-di-tert.butyl-4-hydroxyphenyl)-propionate, 0.2 part by weight of calcium stearate and 0.1 part by weight of the stabilizer of the invention.

To ensure as uniform as possible a distribution on the polymer particles the stabilizers were dissolved in a solvent and the solution was added dropwise to the polypropylene powder while stirring and simultaneously exposing the mixture to the radiation of an IR lamp for evaporating the major portion of the solvent. After about 20 minutes, the calcium stearate was added and mixing was continued for another 10 minutes. Solvent residues were removed by drying for 120 minutes at 50° C. in a drying cabinet.

On a Windsor injection molding machine of the type SP 50 plates of the dimensions 60×60×1 mm were molded at 250° C. and test specimens were cut out according to DIN 53 455, form 3, reduced scale 1:3. The test specimens used for comparison were made in analogous manner but without addition of the stabilizer of the invention (test g) and with the use of known stabilizers (tests e and f).

The stability to light of the specimens was tested in a Xenotest-450 apparatus of Original Hanau Quarzlampen GMBH with a combination of 6 IR and 1 UV filters according to DIN 53 387 (accelerated test of weathering resistance). During the exposure to light the blackpanel temperature was 43° C.±1° C. and the relative humidity in the test chamber was 70±1%. Every 2 hours fresh air was passed through the test chamber for 5 minutes. The elongation at break was determined on a tensile tester of Messrs. Instrom at a draw off speed of 5 cm/min after a defined period of radiation. The test results are listed in the following table.

The stability factor results from the relation of the time of exposure of the stabilized test specimen to the time of exposure of the non stabilized test specimen, in each case after a time of radiation after which the elongation at break had dropped to one half of its initial value.

| Test | stabilizer of Example | stability factor |
|---|---|---|
| (a) | 5 | 4.5 |
| (b) | 8 | 4.5 |
| (c) | 19 | 5.0 |
| (d) | 21 | 5.0 |
| (e) | benzophenone stabilizer [1] | 2.5 |
| (f) | benzotriazole stabilizer [2] | 2.5 |

-continued

| Test | stabilizer of Example | stability factor |
|---|---|---|
| (g) | control (without stabilizer) | 1 |

[1] 2-hydroxy-4-n-octyloxybenzophenone
[2] 2-(2-hydroxy-3',5'-di-tert.butylphenyl-5-chlorobenzotriazole

What is claimed is:

1. Urea derivatives of the formula (I)

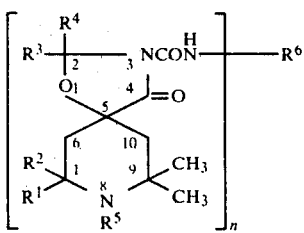

in which
R[1] and R[2] denote identical or different straight chain or branched alkyl radicals having from 1 to 12 carbon atoms, or R[1] and R[2] together with the carbon atom to which they are linked denote a cyclopentane or cyclohexane ring which may be methyl-substituted or a 2,2,6,6-tetramethylpiperidine ring carbon atom 4 of which is identical with carbon atom 7 of the spirodecane system;
R[3] denotes hydrogen, alkyl or isoalkyl having from 1 to 30 carbon atoms, or aralkyl having from 7 to 10 carbon atoms;
R[4] denotes hydrogen, alkyl having from 1 to 30 carbon atoms, phenyl or naphthyl which may be substituted by a halogen atom, or alkyl having from 1 to 4 carbon atoms, or denotes aralkyl with 7 to 10 carbon atoms, or
R[3] and R[4] may also be together with the carbon atom by which they are linked a cycloalkane ring having from 4 to 20 carbon atoms which may be substituted by $C_1$ to $C_4$ alkyl radicals;
R[5] denotes hydrogen, oxygen or $C_1$-$C_4$ alkyl;
n is 1 or 2 depending on the valence of R[6],
R[6], with n being 1, denotes alkyl having from 1 to 20 carbon atoms, alkenyl having from 2 to 18 carbon atoms, cycloalkyl having from 5 to 12 carbon atoms which may be substituted by a $C_1$-$C_4$-alkyl radical; phenyl or naphthyl which may be substituted by a chlorine atom or alkyl having from 1 to 18 carbon atoms; or phenylalkyl having from 7 to 18 carbon atoms, or
R[6], with n being 2, denotes a straight chain or branched alkylene group having from 2 to 20 carbon atoms, or phenylene or naphthylene which may be substituted by $C_1$-$C_4$ alkyl, or a diphenylenealkane radical having from 13 to 18 carbon atoms.

2. Compounds as claimed in claim 1, in which R[1] and R[2] denote methyl and R[5] denotes hydrogen.

3. Process for the manufacture of compounds as claimed in claim 1, which comprises reacting a compound of the formula III

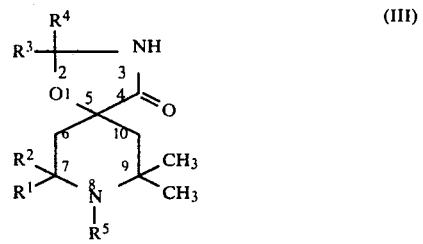

in an inert organic solvent, at a temperature of 20° to 80° C. and with the addition of catalytic amount of a base, with an isocyanate of the formula II $$R_6(NCO)_n \qquad (II)$$

in which formulae R[1], R[2], R[3], R[4], R[5], R[6] and n are as defined in claim 1.

4. Synthetic polymers stabilized against UV decomposition containing from 0.01 to 5 parts by weight, calculated on the polymer, of a compound as claimed in claim 1 or 2, either per se or in the form of a salt with a non oxidizing inorganic or organic acid.

5. Process for stabilizing synthetic polymers against the detrimental influence of light, which comprises adding to the polymer to be stabilized from 0.01 to 5 parts by weight, calculated on the polymer, of a compound as claimed in claim 1, per se or in the form of a salt with a non oxidizing inorganic acid or an organic acid.

* * * * *